United States Patent

Terada et al.

Patent Number: 5,679,674
Date of Patent: Oct. 21, 1997

[54] OPTICALLY ACTIVE THIOMORPHOLINE DERIVATIVES

[75] Inventors: Atsusuke Terada; Yoshio Iizuka; Kazuyuki Wachi; Kenji Fujibayashi, all of Tokyo, Japan

[73] Assignee: Sankyo Company, Limited, Tokyo, Japan

[21] Appl. No.: 387,897

[22] PCT Filed: Aug. 27, 1993

[86] PCT No.: PCT/JP93/01210

§ 371 Date: Feb. 22, 1995

§ 102(e) Date: Feb. 22, 1995

[87] PCT Pub. No.: WO94/05646

PCT Pub. Date: Mar. 17, 1994

[30] Foreign Application Priority Data

Aug. 28, 1992 [JP] Japan ................................. 4-229970

[51] Int. Cl.$^6$ ...................... C07D 417/06; A61K 31/54
[52] U.S. Cl. ............................... 514/227.8; 544/60
[58] Field of Search ...................... 544/60; 514/227.8

[56] References Cited

U.S. PATENT DOCUMENTS 5,021,413   6/1991   Terada et al. ................... 514/227.5

FOREIGN PATENT DOCUMENTS 3-163068   7/1991   Japan.

*Primary Examiner*—Matthew V. Grumbling
*Attorney, Agent, or Firm*—Frishauf, Holtz, Goodman, Langer & Chick, P.C.

[57] ABSTRACT

Optically active carboxamide derivatives having analgesic activity and being useful as an analgesic agent. The compounds have a general formula:

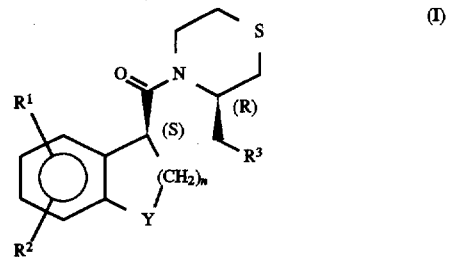

(in the above formula, $R^1$ represents a hydrogen or halogen atom;
$R^2$ represents a halogen atom;
$R^3$ represents a pyrrolidino or piperidino group;
Y represents a methylene or carbonyl group; and
n is an integer of 1 or 2) and pharmacologically acceptable salts thereof.

3 Claims, No Drawings

OPTICALLY ACTIVE THIOMORPHOLINE DERIVATIVES

This is the national stage (35 USC 371) of PCT/JP93/01210, filed Aug. 27, 1993.

TECHNICAL FIELD

The present invention relates to optically active carboxamide derivatives having potent analgesic activity and low toxicity, or to pharmacologically acceptable salts thereof.

BACKGROUND ART

In the central nervous system, the presence of three kinds of receptors, μ-, k- and δ-receptors, participating in analgesic effect has been clarified. It is said that an agonist which has an affinity to k-receptor among these shows strong analgesic effect and does not show such side effects as addiction, tolerance formation, respiratory inhibition, inhibition of smooth muscle movement and so on which are observed, for example, in μ-receptor agonistic morphine etc. Accordingly, the development of a k-receptor agonist having a strong analgesic activity and fewer side effects has been desired.

The present inventors have synthesized a series of heterocyclic compounds and examined their pharmacological activities for many years. As a result, they have found carboxamide derivatives or their pharmacologically acceptable salts thereof having potent analgesic activity and filed a Japanese patent application [JP Kokai Hei 3-163068 (Hei 3. July 15)].

BRIEF DESCRIPTION OF INVENTION

The present inventors have found that optically active carboxamide derivatives having specific stereochemical configuration of the compounds covered in the above application exhibit much strong analgesic activity as k-receptor agonist comparing with racemates and the other stereoisomers have fewer side effects and are practical as analgesic agents; and have accomplished the present invention.

DETAILED DESCRIPTION OF INVENTION

The optically active carboxamide derivatives of the present invention have general formula:

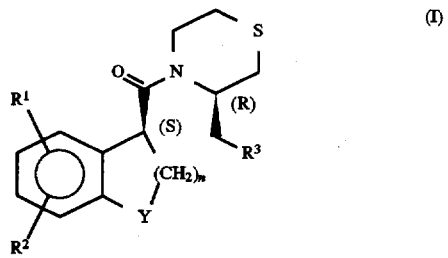

In the formula, $R^1$ represents a hydrogen or halogen atom; $R^2$ represents a halogen atom: $R^3$ represents a pyrrolidino or piperidino group: Y represents a methylene or carbonyl group; and n is an integer of 1 or 2.

An analgesic agent or a k-receptor agonistic agent of the present invention comprises the above compounds or pharmacologically acceptable salts thereof as an active ingredient.

Halogen atoms represented by $R^1$ and $R^2$ include, for example, fluorine, chlorine, bromine and iodine atoms; preferably a fluorine or chlorine atom: and particularly preferably a chlorine atom.

The compounds having a general formula (I) described above can, if necessary, be converted to pharmacologically acceptable salts thereof by conventional means.

Examples of such salts include: for example, salts of mineral acids such as hydrochloric acid, hydroboromic acid, hydroiodic acid, sulfuric acid or phosphoric acid; and salts of organic acids such as methanesulfonic acid, ethanesulfonic acid, benzenesulfonic acid, p-toluenesulfonic acid, oxalic acid, fumaric acid, maleic acid, succinic acid, mandelic acid, citric acid or tartaric acid; and preferably salts of hydrochloric acid, methanesulfonic acid, fumaric acid or succinic acid.

The preferred compounds of general formula (I) are those in which:

(1) $R^1$ is a hydrogen, fluorine or chlorine atom;

(2) $R^2$ is a fluorine or chlorine atom;

(3) $R^3$ is a pyrrolidino group;

(4) Y is a methylene group; and (5) n is 1;

the more preferred compounds of general formula (I) are those in which:

(6) $R^1$ is a hydrogen or chlorine atom; and (7) $R^2$ is a chlorine atom; and the particularly preferred compounds of general formula (I) are those in which:

(8) $R^1$ is a chlorine atom.

The preferred specific compounds are those of Compound No. 1, 2, 3, 4, 5, 6, 7, 8, 9, 17, 19, 33, 41, 42, 43, 44, 57 and 59 in which the Compound Number is same as in Table 3 described hereinafter.

And the more preferred specific compounds are those of
Compound No. 1: (3R)-3-(1-pyrrolidinylmethyl)-4-[(1S)-5,6-dichloro-1-indanecarbonyl]thiomorpholine;
Compound No. 3: (3R)-3-(1-pyrrolidinylmethyl)-4-[(1S)-3-oxo-5,6-dichloro-1-indanecarbonyl]thiomorpholine;
Compound No. 4: (3R)-3-(1-pyrrolidinylmethyl)-4-[(1S)-6,7-dichloro-4(3H)-oxo-1,2-dihydro-1-naphthoyl]thiomorpholine;
Compound No. 6: (3R)-3-(1-piperidinylmethyl)-4-[(1S)-6,7-dichloro-1,2,3,4-tetrahydro-1-naphthoyl]thiomorpholine;
Compound No. 8: (3R)-3-(1-piperidinylmethyl)-4-[(1S)-6,7-dichloro-4(3H)-oxo-1,2-dihydro-1-naphthoyl]thiomorpholine; and
Compound No. 43: (3R)-3-(1-pyrrolidinylmethyl)-4-[(1S)-3-oxo-5-chloro-1-indanecarbonyl]thiomorpholine.

The compounds of a general formula (I) of the present invention can readily be prepared by the following method:
[Method A]

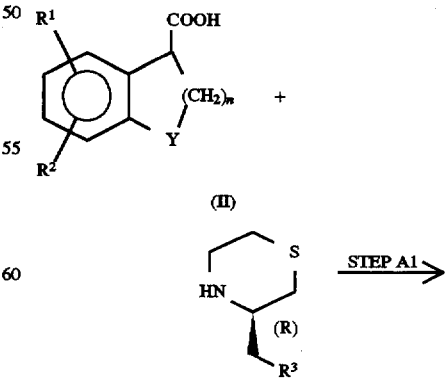

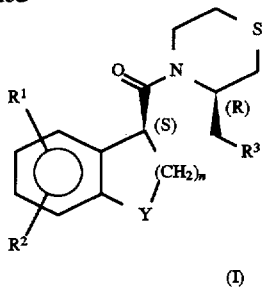

(I)

In the above formulae, $R^1$, $R^2$, $R^3$, Y and n are as defined above.

Method A involves a method for preparing a compound of formula (I).

Step A1 is a step for preparing a compound of general formula (I) and is conducted by reacting a compound of general formula (II) or its reactive derivative with a compound of general formula (III) in an inert solvent and then by resolving the isomeric mixtures produced.

The reaction of a compound of formula (II) or its reactive derivative with a compound of formula (III) is carried out by, for example, an acid halide method, a mixed acid anhydride method, an activated ester method or a condensing method.

An acid halide method is conducted by reacting a compound of formula (II) with a halogenating agent (for example, thionyl chloride, phosphorus pentachloride and the like) to prepare an acid halide and then by reacting with a compound of formula (III) in an inert solvent in the presence or absence of a base.

The bases used include for example: organic amines such as triethylamine, N-methylmorpholine, pyridine, 4-dimethylaminopyridine and 1,8-diazabicyclo-[5.4.0] undec-7-ene (DBU); alkali metal hydrogencarbonates such as sodium hydrogencarbonate or potassium hydrogencarbonate; alkali metal carbonates such as sodium carbonate or potassium carbonate: and alkali metal hydroxides such as sodium hydroxide or potassium hydroxide; and preferably organic amines.

There is no particular limitation upon the nature of the inert solvent used, provided that it has no adverse effect upon the reaction. Such solvents include, for example: hydrocarbons such as hexane, cyclohexane, benzene, toluene or xylene; halogenated hydrocarbons such as dichloromethane, chloroform, carbon tetrachloride or 1,2-dichloroethane; ethers such as ether, tetrahydrofuran or dioxane; ketones such as acetone; amides such as N,N-dimethylformamide, N,N-dimethylacetamide, N-methyl-2-pyrrolidone or hexamethylphosphoramide; and sulfoxides such as dimethyl sulfoxide; and preferably halogenated hydrocarbons or ethers.

The reaction temperature depends upon the nature of starting compounds of formulae (II) and (III) as well as the nature of the solvent, but the temperature for both reactions of the compound of formula (II) with a halogenating agent and of the acid halide with a compound of formula (III) is normally −20° to 150° C.; and preferably about room temperature for the reaction of the compound of formula (II) with a halogenating agent and 0° to 100° C. for the reaction of the acid halide with a compound of formula (III).

The reaction time varies depending upon the reaction temperature and other conditions, but it is normally 30 minutes to 24 hours (preferably 1 to 10 hours).

A mixed acid anhydride method is conducted by reacting a compound of formula (II) with a $C_1$–$C_4$-alkyl halocarbonate such as ethyl chloroformate or isobutyl chloroformate to prepare an mixed acid anhydride and then by reacting with a compound of formula (III).

Reaction for preparing the mixed acid anhydride is carried out by reacting a compound of formula (II) with a $C_1$–$C_4$-alkyl halocarbonate; and preferably in an inert solvent in the presence of a base.

The base and the inert solvent used are similar to those used in the said acid halide method.

The reaction temperature depends upon the nature of a starting compound of formula (II) and the nature of the solvent used, but the temperature is normally −20° to 50° C. (preferably 0° to 30° C.). The reaction time varies depending upon the reaction temperature and other conditions, but it is normally 30 minutes to 24 hours (prefereably 1 to 10 hours).

The reaction of a compound of formula (III) with the mixed acid anhydride is preferably carried out in an inert solvent in the presence or absence of a base. The base and the inert solvent used are similar to those used in the said acid halide method.

The reaction temperature depends upon the nature of a starting compound of formula (III) as well as the nature of the solvent used, but the temperature is normally −20° to 100° C. (preferably from 0° to room temperature). The reaction time varies depending upon the reaction temperature and other conditions, but it is normally 30 minutes to 24 hours (preferably 1 to 10 hours).

This method is preferably conducted in the presence of compound of formula (II), compound of formula (III) and a $C_1$–$C_4$-alkyl halocarbonate without isolation of the mixed acid anhydride.

An activated ester method is conducted by reacting a compound of formula (II) with an active esterifying agent (for example, N-hydroxy compounds such as N-hydroxysuccinimide, N-hydroxybenzotriazole or the like) in the presence of a condensing agent (for example, dicyclohexylcarbodiimide, carbonyldiimidazole and the like); or by reacting a compound of formula (II) with an active esterifying agent [for example, di($C_1$–$C_4$-alkyl) cyanophosphonates such as diethyl cyanophosphonate, diarylphosphoryl azides such as diphenylphosphoryl azide or dinaphthylphosphoryl azide and the like] to prepare an activated ester and then by reacting with a compound of formula (III).

Reaction for preparing an activated ester is preferably carried out in the presence of an inert solvent. The inert solvent used for the reaction is similar to those used in the said acid halide method.

The reaction temperature depends upon the nature of starting compounds of formulae (II) and (III) as well as the nature of the solvent used, but the temperature for the active esterifying reaction is normally −20° to 50° C. (preferably −10° to 30° C.). The reaction temperature for the reaction of an activated ester compound with a compound of formula (III) is −20° to 50° C. (preferably 0° to 30° C.). The reaction time for both reactions varies depending upon the reaction temperature and other conditions, but the time for both reactions is 30 minutes to 24 hours (preferably 1 to 10 hours).

This method is preferably carried out in the presence of compound of formula (II), compound of formula (III) and an active esterifying agent without isolation of an activated ester.

A condensing method is carried out by reacting directly a compound of formula (II) with a compound of formula (III) in the presence of a condensing agent (for example, dicyclohexylcarbodiimide, carbonyldiimidazole, 1-(N,N-dimethylaminopropyl)-3-ethylcarbodiimide hydrochloride, triphenylphosphine-2,2'-dipyridinyl disulfide and the like). This reaction is carried out in a similar manner to that of the said activated ester method.

After completion of the reaction, the desired compounds in each step can be recovered from the reaction mixture by conventional means. For example, precipitated crystals are collected by filtration: or water is added to the reaction mixture, the resulting mixture is extracted with a water-immiscible organic solvent such as ethyl acetate, the extract is dried and the solvent of the extract is removed by distillation. The product, if necessary, can be further purified by conventional means, for example, recrystallization, column chromatography or the like.

Resolution of the isomeric mixtures produced above can be carried out by conventional means for optical resolution. For example, optical isomers can be resolved by column chromatography through silica gel using a (50–100):1 mixture of ethyl acetate and triethylamine as a mobile phase.

The desired compound of formula (I) can also be prepared by reacting an optically active compound of general formula (IIa), which is obtained by the optical resolution of a compound of formula (II), with a compound of formula (III).

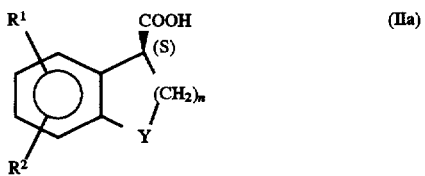

The optical resolution of a compound of formula (II) is carried out by conventional means. For example, the optical resolution is carried out by using brucine as an agent for resolution and by recrystallizing from a mixture of an ether such as ethyl ether or isopropyl ether (preferably isopropyl ether) and a ketone (preferably acetone).

The reaction of a compound of formula (IIa) with a compound of formula (III) is carried out in a similar manner to the above reaction of a compound of formula (II) with a compound of formula (III); and preferably by the mixed acid anhydride method, activated ester method or condensing method.

The starting compound of formula (II) used in Method A is either known or can be easily produced according to known methods (for example, Japanese Patent Kokai No. Hei 2-149560).

(Effect of Invention)

The compounds having the general formula (I) mentioned already have a potent analgesic activity as shown below and have no such side effects as addiction, tolerance formation, respiratory inhibition and inhibition of smooth muscle movement. Therefore, the compounds are very useful as an analgesic agent.

(TEST EXAMPLE 1)

p-Phenylquinone-induced agony test in mice (hypodermic administration)

According to the method of Siegmund et al. [Proc. Soc. Exptl. Biol. Med., 95, 729 (1957)], the title test was conducted.

Male ddy mice (Japan SLC) each weighing about 20 g were fasted for about 16 hours from the day before the test and divided into groups each including from 5 to 10 mice.

A compound to be tested was dissolved in physiological saline and administered by subcutaneous injection. After 15 minutes, 0.1 ml/mouse of 0.03% p-phenylquinone solution was injected intraperitoneally. During 5 to 10 minutes after injection, the number of agony reactions (writhing response) observed in each mouse was counted. Those mice showing ½ or less of the mean value of the numbers of agony reactions observed in the control mice injected with only physiological saline were regarded as analgesic-effective animals. The ratio of the number of analgesic-effective animals to the number of animals used was obtained for each dose and $ED_{50}$ (50% effective dose) was calculated according to the probit method.

(TEST EXAMPLE 2)

Receptor-affinity test (1) Preparation of raw cerebro-membranous preparation

According to the method of Pasuternak et al. [Mol. Pharmacol., 11, 340 (1975)], preparative procedure was performed. The whole brain of male Hertley guinea pigs (Japan SLC) each weighing from 400 to 700 g, from which the cerebellium was removed, was homogenized in 30 parts of ice-cooled 50 mM tris buffer (pH 7.4) by use of Polytron and then centrifuged for 15 minutes at 49,000× g. Precipitated pellet was suspended again in the same kind of buffer as above. The suspension was incubated at 37° C. for 30 minutes, and then centrifuged under the same conditions as above. The precipitate was suspended in 30 parts of the buffer and preserved at −80° C. This raw preparation was molten before use, homogenized by use of a Downs-type homogenizer and then diluted for the final protein concentration to be 0.5 mg/ml.

(2) Binding to k-receptor

According to the method of Magnan et al. [Arch. Pharmacol. 319, 197 (1982)], the binding test was performed. As the ligand, 0.6 nM of tritium-labelled ethylketocyclazocine was used. Its binding to the cerebro-membranous preparation was tested under the conditions that μ- and δ-receptors were saturated with 100 nM DAGO (D-Ala$^2$, MePhe$^4$, Gly-oL$^5$-enkephalin) and with 10 nM DADLE [(D-Ala$^2$, D-Leu$^5$)-enkephalin]. The cerebro-membranous preparation, labelled and unlabelled ligands, and a compound to be tested were incubated in 1 ml of tris buffer solution at 25° C. for 45 minutes. Then, 5 ml of the buffer solution previously ice-cooled were added to the mixture, filtered under a reduced pressure through a Warmann GF/B filter paper and washed twice. The labelled ligand bound to the filter paper was added with emulsified scintillator (ACS-11), allowed to stand overnight and then measured by a liquid scintillation counter. The affinity of a test compound to the receptor was indicated by the concentration which inhibited binding of the labelled ligand by 50% ($IC_{50}$, nM).

(3) Binding to μ-receptor

According to the method of Magnan et al. mentioned above, the binding test was performed. By use of 1 nM of tritium-labelled DAGO as the ligand, the test was carried out by a similar procedure to the binding test for k-receptor. The affinity of a test compound to the receptor was indicated in the same way as the above.

Table 1 shows the results of Test Examples 1 and 2.

TABLE 1

| Compounds | Analgesic effect ($ED_{50}$, μg/kg sc) Phenylquinone-induced agony test | Binding to the receptors ($IC_{50}$, nM) | |
|---|---|---|---|
| | | k | μ |
| Compound of Example 1 (3R, 1S) | 1.3 | 0.44 | 300 |
| Corresponding (3S, 1R) | 10900 | 21000 | 12000 |

TABLE 1-continued

| Compounds | Analgesic effect (ED$_{50}$, µg/kg sc) Phenylquinone-induced agony test | Binding to the receptors (IC$_{50}$, nM) | |
|---|---|---|---|
| | | k | µ |
| Corresponding (3R, 1R) | 23900 | 3500 | 32000 |
| Corresponding (3S, 1S) | 7800 | 920 | 15000 |
| Compound of Example 2 | 0.6 | 0.46 | 330 |
| Compound of Example 3 | 13.0 | 1.70 | 1800 |
| Compound A*) | 490 | 9.92 | 636 |
| Morphine HCl | 480 | 552 | 5.1 |

Compound A: trans-N-[2-(1-Pyrrolidinyl)cyclohexyl]-N-methyl-2-(3,4-dichlorophenyl)acetamide (TEST EXAMPLE 3)

p-Phenylquinone-induced agony test in mice (oral administration)

According to the method of Siegmund et al. [Proc. Soc. Exptl. Biol. Med., 95, 729 (1957)], the title test was conducted. Male ddy mice (Japan SLC) each weighing about 20 g were fasted for about 16 hours from the day before the test and divided into groups each including from 5 to 10 mice.

A compound to be tested was dissolved in 0.5% tragacanth and administered orally. After 15 minutes, each 0.1 ml/mouse of 0.03% p-phenylquinone solution was injected intraperitoneally. During 5 to 10 minutes after injection, the number of agony reactions (writhing response) observed in each mouse was counted. Those mice showing ½ or less of the mean value of the numbers of agony reactions observed in the control mice injected with only physiological saline were regarded as analgesic-effective animals. The ratio of the number of analgesic-effective animals to the number of animals used was obtained for each dose and ED$_{50}$ (50% effective dose) was calculated according to the probit method.

Table 2 shows the results of Test Example 3.

TABLE 2

| Compounds | Analgesic effect (Oral Administration) (ED$_{50}$, mg/kg) Phenylquinone-induced agony test |
|---|---|
| Compound of Example 1 | 0.011 |
| Racemate Corresponding to Compound of Example 1 | 0.18 |
| Compound of Example 2 | 0.031 |
| Racemate Corresponding to Compound of Example 2 | 0.79 |
| Compound of Example 3 | 0.29 |
| Racemate Corresponding to Compound of Example 3 | 1.22 |

[Possible Exploitation in Industry]

In a case where compounds of formula (I) is used as an analgesic agent, the compounds or a mixture of the compounds with pharmacologically acceptable carriers, excipients, diluents and the like can conveniently be administered orally or non-orally (intravenously, intramuscularly, intestinally etc.) as pharmaceutical compositions such as powder, granule, tablet, capsule, syrup, injection, suppository, ointment, cream, plaster and the like. The dose varies depending upon the symptoms of the patient and upon the type of administration but the compounds, in general, can be administered in a daily dose of about 0.001 to 100 mg, particularly about 0.01 to 10 mg in the case of oral administration or in a daily dose of about 0.001 to 10 mg, particularly about 0.002 to 5 mg in the case of intravenous or intramuscular administration, either as a single dose or as divided doses.

[The Best Mode for carrying out the invention]

The following Examples and Referential Examples are provided in order that the present invention can be more fully understood. Such examples are not to be construed as being limitative of the invention.

(EXAMPLE 1)

(3R)-3-(1-Pyrrolidinylmethyl)-4-[(1S)-(5,6-dichloro-1-indanecarbonyl]thiomorpholine hydrochloride A solution of 2.74 g of 1-(5,6-dichloroindane)carboxylic acid chloride in 30 ml of dichloromethane was added dropwise to a solution of 1.96 g of (R)-3-(1-pyrrolidinyl) methylthiomorpholine and 1.67 ml of triethylamine in 30 ml of dichloromethane at −10° C. under a stream of nitrogen. The resulting mixture was stirred at the same temperature for 20 minutes and then at room temperature for an hour and a half. The reaction mixture was poured into a saturated aqueous solution of sodium hydrogencarbonate and extracted with dichloromethane. The extract was washed with a saturated aqueous solution of sodium chloride and dried over anhydrous sodium sulfate. After the solvent was distilled off, the residue was purified by column chromatography through silica gel using a 50:1 mixture of ethyl acetate and triethylamine as a mobile phase to give 1.52 g of the free basic form of the title compound from the less polar fractions. The product was added to a solution of excess hydrogen chloride in dioxane and the solution was stirred at room temperature for 30 minutes. The solvent was distilled off to give 1.55 g of the title compound. m.p.: 245°–248° C. $[\alpha]_D^{25}$ +2.0° (c=1.0, methanol)

Anal. Calcd. for $C_{20}H_{25}Cl_3N_2OS$: C, 52.36%; H, 5.78%: Cl, 24.40%: N, 6.43%; S, 7.36% Found: C, 52.40%; H, 5.79%; Cl, 24.33%; N, 6.39%; S, 7.18%

From the more polar fraction in the above column chromatography, there were obtained 1.09 g of the free basic form of the (R,R)-optical isomer of the title compound. This product was treated with hydrogen chloride in a similar manner to above to give 1.12 g of the optical isomer of the title compound. m.p.: 230°–232° C. $[\alpha]_D^{25}$ −125.4° (c=1.0, methanol)

Anal. Calcd. for $C_{20}H_{25}Cl_3N_2OS$: C, 52.36%; H, 5.78%: Cl, 24.40%; N, 6.43%; S, 7.36% Found: C, 52.39%; H, 5.73%; Cl, 24.18%; N, 6.42%; S, 7.54%

(EXAMPLE 2)

(3R)-3-(1-Pyrrolidinylmethyl)-4-[(1S)-3-oxo-5,6-dichloro-1-indanecarbonyl]thiomorpholine hydrochloride A similar reaction to that of Example 1 was carried out by using 1.0 g of (3R)-3-(1-pyrrolidinyl) methylthiomorpholine, 2.0 ml of triethylamine and 3.0 g of 3-oxo-5,6-dichloro-1-indanecarboxylic acid chloride and the crude product was purified by column chromatography through silica gel using a 100:1 mixture of ethyl acetate and triethylamine as a mobile phase to give 0.82 g of the free basic form of the title compound from the less polar fractions. The product was treated with hydrogen chloride in a similar manner to the latter part of Example 1 to give 0.85 g of the title compound. m.p.: 257°–261° C. $[\alpha]_D^{25}$ +26.8° (c=2.0, methanol)

Anal. Calcd. for $C_{19}H_{23}Cl_3N_2O_2S$: C, 50.73%; H, 5.15%; Cl, 23.64%; N, 6.23%; S, 7.13% Found: C, 50.48%; H, 5.20%; Cl, 23.49%; N, 6.16%; S, 7.09%

From the more polar fractions in the above column chromatography, there were obtained 0.99 g of the free basic form of the (R,R)-optical isomer of the title compound. This product was treated with hydrogen chloride in a similar manner to the latter part of Example 1 to give 1.00 g of the optical isomer of the title compound. m.p.: 247°–249° C. $[\alpha]_D^{25}$ −107.2° (c=2.0, methanol)

Anal. Calcd. for $C_{19}H_{23}Cl_3N_2O_2S$: C, 50.73%; H, 5.15%; Cl, 23.64%; N, 6.23%; S, 7.13% Found: C, 50.69%; H, 5.33%; Cl, 23.54%; N, 6.17%; S, 7.24%

(EXAMPLE 3)

(3R)-3-(1-Piperidinylmethyl)-4-[(1S)-6,7-dichloro-4 (3H)-oxo-1,2-dihydro-1-naphthoyl]thiomorpholine hydrochloride A similar reaction to that of Example 1 by using 2.0 g of (R)-3-(1-piperidinylmethyl)thiomorpholine, 1.7 ml of triethylamine and 3.1 g of 1-(4-oxo-6,7-dichlorotetralone) carboxylic acid chloride and the crude product was purified by column chromatography using a 100:1 mixture of ethyl acetate and triethylamine as a mobile phase to give 1.6 g of the free basic form of title compound from the less polar fractions. This product was treated with hydrogen chloride in a similar manner to the latter part of Example 1 to give 1.65 g of the title compound. m.p.: 255°–258° C. $[\alpha]_D^{25}$ −87.3° (c=1.0, methanol)

Anal, Calcd. for $C_{22}H_{27}Cl_3N_2O_2S$: C, 52.78%; H, 5.70%; Cl, 22.26%; N, 5.86%; S, 6.71% Found: C, 52.58%; H, 5.76%: Cl, 22.15%; N, 5.76%; S, 6.94%

From the more polar fractions in the above column chromatography there were obtained 1.1 g of the free basic form of the (R,R)-optical isomer of the title compound. The product was treated with hydrogen chloride in a similar manner to the latter part of Example 1 to give 1.05 g of the optical isomer of the title compound. m.p.: 245°–248° C. $[\alpha]_D^{25}$ −21.8° (c=1.0, methanol)

Anal. Calcd. for $C_{22}H_{27}Cl_3N_2O_2S$: C, 52.78%; H, 5.70%; Cl, 22.26%; N, 5.86%; S, 6.71% Found: C, 52.49%; H, 5.88%; Cl, 22.11%; N, 5.65%; S, 6.67%

(EXAMPLE 4)

(3R)-3-(1-pyrrolidinylmethyl)-4-[(1S)-5,6-dichloro-1-indanecarbonyl)thiomorpholine 9.0 ml of triethylamine were added dropwise to a solution of 14.7 g of (S)-5,6-dichloroindanecarboxylic acid in 200 ml of tetrahydrofuran at −25° to −20° C. under a stream of nitrogen and then a solution of 10.9 g of (R)-3-(1-pyrrolidinylmethyl)thiomorpholine in 50 ml of tetrahydrofuran was added dropwise thereto at the same temperature. After the solution was stirred for 10 minutes, a solution of 10.5 g of diethyl cyanophosphonate in 50 ml of tetrahydrofuran was added dropwise to the above solution and stirred at the same temperature for 30 minutes and then at 0° to 5° C. for an hour. After the tetrahydrofuran was distilled off, an aqueous solution of sodium hydrogencarbonate was added to the residue and extracted with ethyl acetate. The extract was washed with water and dried over anhydrous sodium sulfate. After the organic solvent was distilled off, the residue was recrystallized from a mixture of ethyl acetate and hexane to give 13.1 g of the title compound. m.p.: 123°–124° C.

Anal. Calcd. for $C_{19}H_{24}Cl_2N_2OS$: C, 57.14%; H, 6.06%: N, 7.01%; Cl, 17.75%: S, 8.03% Found: C, 57.28%: H, 6.09%; N, 7.04%; Cl, 17.78%: S, 8.30%

According to similar procedures to those in Examples 1–4, the preferred compounds shown in the following Table 3 can be prepared.

TABLE 3

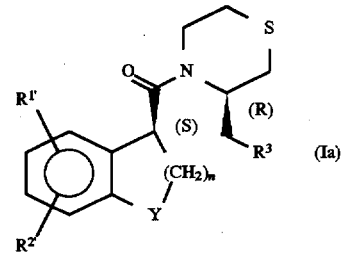

| Compd. No. | $R^{1'}$ | $R^{2'}$ | $R^3$ | Y | n |
|---|---|---|---|---|---|
| 1 | Cl | Cl | Pyr | $CH_2$ | 1 |
| 2 | Cl | Cl | Pyr | $CH_2$ | 2 |
| 3 | Cl | Cl | Pyr | CO | 1 |
| 4 | Cl | Cl | Pyr | CO | 2 |
| 5 | Cl | Cl | Pip | $CH_2$ | 1 |
| 6 | Cl | Cl | Pip | $CH_2$ | 2 |
| 7 | Cl | Cl | Pip | CO | 1 |
| 8 | Cl | Cl | Pip | CO | 2 |
| 9 | Cl | F | Pyr | $CH_2$ | 1 |
| 10 | Cl | F | Pyr | $CH_2$ | 2 |
| 11 | Cl | F | Pyr | CO | 1 |
| 12 | Cl | F | Pyr | CO | 2 |
| 13 | Cl | F | Pip | $CH_2$ | 1 |
| 14 | Cl | F | Pip | $CH_2$ | 2 |
| 15 | Cl | F | Pip | CO | 1 |
| 16 | Cl | F | Pip | CO | 2 |
| 17 | Cl | H | Pyr | $CH_2$ | 1 |
| 18 | Cl | H | Pyr | $CH_2$ | 2 |
| 19 | Cl | H | Pyr | CO | 1 |
| 20 | Cl | H | Pyr | CO | 2 |
| 21 | Cl | H | Pip | $CH_2$ | 1 |
| 22 | Cl | H | Pip | $CH_2$ | 2 |
| 23 | Cl | H | Pip | CO | 1 |
| 24 | Cl | H | Pip | CO | 2 |
| 25 | Cl | Br | Pyr | $CH_2$ | 1 |
| 26 | Cl | Br | Pyr | $CH_2$ | 2 |
| 27 | Cl | Br | Pip | $CH_2$ | 1 |
| 28 | Cl | Br | Pip | $CH_2$ | 2 |
| 29 | Cl | I | Pyr | $CH_2$ | 1 |
| 30 | CL | I | Pyr | $CH_2$ | 2 |
| 31 | Cl | I | Pip | $CH_2$ | 1 |
| 32 | Cl | I | Pip | $CH_2$ | 2 |
| 33 | F | Cl | Pyr | $CH_2$ | 1 |
| 34 | F | Cl | Pyr | $CH_2$ | 2 |
| 35 | F | Cl | Pyr | CO | 1 |
| 36 | F | Cl | Pyr | CO | 2 |
| 37 | F | Cl | Pip | $CH_2$ | 1 |
| 38 | F | Cl | Pip | $CH_2$ | 2 |
| 39 | F | Cl | Pip | CO | 1 |
| 40 | F | Cl | Pip | CO | 2 |
| 41 | H | Cl | Pyr | $CH_2$ | 1 |
| 42 | H | Cl | Pyr | $CH_2$ | 2 |
| 43 | H | Cl | Pyr | CO | 1 |
| 44 | H | Cl | Pyr | CO | 2 |
| 45 | H | Cl | Pip | $CH_2$ | 1 |
| 46 | H | Cl | Pip | $CH_2$ | 2 |
| 47 | H | Cl | Pip | CO | 1 |
| 48 | H | Cl | Pip | CO | 2 |
| 49 | Br | Cl | Pyr | $CH_2$ | 1 |

TABLE 3-continued structure (Ia)

| Compd. No. | $R^{1'}$ | $R^{2'}$ | $R^3$ | Y | n |
|---|---|---|---|---|---|
| 50 | Br | Cl | Pyr | $CH_2$ | 2 |
| 51 | Br | Cl | Pip | $CH_2$ | 1 |
| 52 | Br | Cl | Pip | $CH_2$ | 2 |
| 53 | I | Cl | Pyr | $CH_2$ | 1 |
| 54 | I | Cl | Pyr | $CH_2$ | 2 |
| 55 | I | Cl | Pip | $CH_2$ | 1 |
| 56 | I | Cl | Pip | $CH_2$ | 2 |
| 57 | F | F | Pyr | $CH_2$ | 1 |
| 58 | F | F | Pyr | $CH_2$ | 2 |
| 59 | F | F | Pyr | CO | 1 |
| 60 | F | F | Pyr | CO | 2 |
| 61 | F | F | Pip | $CH_2$ | 1 |
| 62 | F | F | Pip | $CH_2$ | 2 |
| 63 | F | F | Pip | CO | 1 |
| 64 | F | F | Pip | CO | 2 |

In the Table the abbreviations used have the following meanings:

Pyr: pyrrolidino group
Pip: piperidino group.

(REFERENTIAL EXAMPLE 1)

(1S)-5,6-Dichloro-1-indanecarboxylic acid 138.4 g of 5,6-dichloro-1-indanecarboxylic acid (0.599 mol) and 257.9 g of brucine dihydrate (0.599 mol) were dissolved in 500 ml of acetone upon heating, and 500 ml of isopropyl ether were added thereto and then allowed to stand overnight. Precipitated crystals were collected by filtration under reduced pressure to give 198.0 g of (1S)-5,6-dichloro-1-indanecarboxylic acid brucine salt. m.p.: 78°–80° C. $[\alpha]_D^{25}$ −27.4° (c=1.0, methanol)

Anal. Calcd. for $C_{33}H_{34}Cl_2N_2O_6 \cdot 3H_2O$: C, 58.32%; H, 5.93%; N, 4.12%; Cl, 10.43% Found: C, 58.03%: H; 5.76%; N, 4.18%; Cl, 10.36%

(1S)-5,6-Dichloroindanecarboxylic acid brucine salt obtained above was dissolved in 250 ml of water and the pH was adjusted to pH 1 with 60 ml of 6 N hydrochloric acid. After the solution was stirred vigorously, a yellow oil liberated was extracted with ethyl acetate. The extract was washed with water and dried over anhydrous magnesium sulfate. The solvent was distilled off to give 68.7 g of the title compound. m.p.: 135°–136° C. $[\alpha]_D^{25}$ −53.5° (c=1.0, methanol)

Anal. Calcd. for $C_{10}H_8Cl_2O_2$: C, 51.98%: H, 3.49%: Cl, 30.68% Found: C, 51.98%; H, 3.59%: Cl, 30.64%

(REFERENTIAL EXAMPLE 2)

(R)-3-(1-Pyrrolidinylmethyl)thiomorpholine 32.6 g of di-t-butyl dicarbonate and 94.2 ml of triethylamine were added to a solution of 0.20 g of thiomorpholine-(R)-3-carboxylic acid in 800 ml of aqueous dioxane (1:1) and the mixture was stirred at room temperature for 3 hours. After the solvent was distilled off, 400 ml of ethyl acetate were added to the residue, which was washed with 70 ml of a saturated aqueous solution of citric acid and dried over anhydrous sodium sulfate. After the solvent was distilled off, the residue was recrystallized from a mixture of ethyl acetate and hexane to give 27.2 g of (N-t-butoxycarbonyl)-thiomorpholine-(R)-3-carboxylic acid. m.p.: 136°–137° C.

10.14 ml of diethyl cyanophosphonate were added to a solution of 12.37 g of the carboxylic acid obtained above, 7.64 ml of triethylamine and 5.01 ml of pyrrolidine in 150 ml of tetrahydrofuran and the mixture was stirred at room temperature for 3 hours. After the solvent was distilled off, the residue was dissolved in ethyl acetate. The solution was washed with a saturated aqueous solution of sodium hydrogencarbonate and dried over anhydrous sodium sulfate. After the solvent was distilled off, the crude crystalline residue was recrystallized from a mixture of ethyl acetate and hexane to give 13.73 g of (N-t-butoxycarbonyl) thiomorpholine-(R)-3-carboxy-(1-pyrrolidinyl)amide. m.p.: 121°–123° C.

12.02 g of the amide derivative obtained above were dissolved in 25 ml of a 4N solution of hydrogen chloride in dioxane and stirred at room temperature for 0.5 hour. The solvent was distilled off to give 6.42 g of thiomorpholine-(R)-3-carboxy-(1-pyrrolidinyl)amide. m.p.: 79°–80° C.

6.00 g of the amide compound obtained above were dissolved in 150 ml of tetrahydrofuran, 3.41 g of lithium aluminium hydride were added thereto and the mixture was stirred at room temperature for 1.0 hour. After completion of the reaction, 30 g of sodium sulfate decahydrate were slowly added to the reaction mixture to stop the reaction. The mixture was filtered and the filtrate was concentrated to give 5.12 g of the title compound. b.p.: 124°–126° C./12 mmHg $[\alpha]_D^{25}$ −42.9° (c=2.0, methanol)

Anal. Calcd. for $C_9H_{18}N_2S$: C, 58.02%: H, 9.74%: N, 15.04%: S, 17.21% Found: C, 57.94%: H, 9.68%: N, 14.78%; S, 17.14%

We claim:

1. (3R)-3-(1-Pyrrolidinylmethyl)-4-[(1S)-5,6-dichloro-1-indanecarbonyl]thiomorpholine or pharmacologically acceptable salts thereof.

2. An analgesic agent comprising (i) a pharmaceutically acceptable carrier; and (ii) an analgesically effective amount of the compound or a pharmaceutically acceptable salt thereof, of claim 1.

3. A k-receptor agonistic agent comprising (i) a pharmaceutically acceptable carrier; and (ii) an effective amount of the compound or pharmaceutically acceptable salt thereof, of claim 1.

* * * * *